US007910570B2

(12) United States Patent
Rubin et al.

(10) Patent No.: US 7,910,570 B2
(45) Date of Patent: Mar. 22, 2011

(54) COMPOSITION COMPRISING A COMBINATION OF AN AROMATASE INHIBITOR, A PROGESTIN AND AN OESTROGEN AND ITS USE FOR THE TREATMENT OF ENDOMETRIOSIS

(75) Inventors: Stephen Rubin, Southampton, NJ (US); Serdar E. Bulun, Chicago, IL (US)

(73) Assignee: AstraZeneca AB, Sodertalje (SE)

( * ) Notice: Subject to any disclaimer, the term of this patent is extended or adjusted under 35 U.S.C. 154(b) by 546 days.

(21) Appl. No.: 10/543,584

(22) PCT Filed: Feb. 3, 2004
(Under 37 CFR 1.47)

(86) PCT No.: PCT/GB2004/000414
§ 371 (c)(1),
(2), (4) Date: Jul. 27, 2005

(87) PCT Pub. No.: WO2004/069260
PCT Pub. Date: Aug. 19, 2004

(65) Prior Publication Data
US 2006/0142256 A1 Jun. 29, 2006

(30) Foreign Application Priority Data
Feb. 5, 2003 (GB) .................... 0302572.3

(51) Int. Cl.
*A01N 45/00* (2006.01)
*A61K 31/56* (2006.01)
(52) U.S. Cl. ........ 514/170; 514/171; 514/178; 514/182; 514/899
(58) Field of Classification Search .............. 514/170, 514/171, 178, 182, 899
See application file for complete search history.

(56) References Cited

U.S. PATENT DOCUMENTS

| 5,183,814 | A | 2/1993 | Dukes |
| 5,550,107 | A * | 8/1996 | Labrie ............... 514/11 |
| 6,265,393 | B1 * | 7/2001 | Heinrichs ............ 514/178 |
| 2002/0156059 | A1 | 10/2002 | Elliesen |
| 2004/0120956 | A1 * | 6/2004 | Song et al. ........... 424/146.1 |

FOREIGN PATENT DOCUMENTS

| EP | 0451869 B1 | 12/1995 |
| WO | 95/17194 A1 | 6/1995 |
| WO | 95/20972 A1 | 8/1995 |
| WO | 99/63973 A2 | 12/1999 |
| WO | 00/07599 A1 | 2/2000 |
| WO | 02/30355 A2 | 4/2002 |
| WO | 02/072106 A2 | 9/2002 |
| WO | 02/074315 A1 | 9/2002 |
| WO | 03/015872 A2 | 2/2003 |
| WO | 03/017973 A1 | 3/2003 |
| WO | 03/017974 A1 | 3/2003 |
| WO | 03/039455 A2 | 5/2003 |
| WO | 03/061665 A1 | 7/2003 |
| WO | 03/082254 A1 | 10/2003 |
| WO | 03/082299 A1 | 10/2003 |
| WO | 03/082336 A1 | 10/2003 |

OTHER PUBLICATIONS

Teirney et al. Reviews in Gynaecological Practice 2 (2002), pp. 91-98.*
Bulun et al. Human Reproduction Update (2002). vol. 6, No. 5,pp. 413-418.*
Taiwan Office Action, 3 pages.
Office Action mailed May 28, 2008 for Application No. 1-2005-501405, Applicant AstraZeneca AB, filed Aug. 1, 2005, Republic of the Phillipines, Intellectual Property Phillipines, Bureau of Patents, Medical Science & Biotechnology Examining Division.
Office Action dated Oct. 1, 2007 for Russian Federation Patent Application No. 2005 127 667, Applicant AstraZeneca AB.
ACOG; Obstet Gynecol, 405-407, 112, (year 2008).
ASRM; Fertility and Sterility, 2006, S18-S27, 86.
ASRM; Fertility and Sterility, 2006, S156-S160, 86.
ASRM; Fertility and Sterility, 1997, 817-821, 67.
Abrao et at; Human Reproduction, 2007, 3092-3097, 22.
Acien et al; Fertility and Sterility, 2007, 32-8, 88.
Ailawadi et al; Fertility and Sterility, 2004, 290-296, 81.
Amsterdam, Fertility and Sterility, 2005, 300-304, 84.
Attar et al; Fertility and Sterility, 2006, 1307-1318, 85.
Attar et al; Comtemp Ob/Gyn, 2006, 82-89.
Attar et al; Human Reprod Update, 2006, 49-56, 12.
Ballard et al; Fertility and Sterility, 2006, 1296-1306, 86.
Bertelsen et al; Ind J Cancer, 2006, 1372-1375, 120.
Bianconi et al; Fertility and Sterility, 2007,1285-1287, 85.
Biberoglu et al; Am J Obstet Gynecol, 1981, 645-654, 139.
Bulun et al; J Clin Endo Metab, 1993, 1458-1463, 76.
Bulun et al; Ann NY Acad Sci, 2002, 75-85, 955.
Bulun et al; J Molec Endocrinol, 2000, 35-42, 25.
Bulun et al; Seminar in Reprod Med, 2004, 45-50, 22.
Bulun et al; Pharmacol Rev, 2005, 359-383, 57.
Bulun et al; Endocrine-Related Cancer, 1999, 293-103, 6.
Bulun et al; Molec Cell Endocrinol, 2006, 94-103, 248.
Carbognin et al; Radiol Med, 2006, 687-701, 111.
Cheng et al; Am J Obstet Gynecol, 2007, e1.391-e8.381, 196.
Child et al; Drugs, 2001, 1735-1750, 61.
Chlouber et al; Expert Opinion Investig Drugs, 2006, 399-407, 15.
Crosignani et al; Human Reprod Update, 2006, 179-189, 12.
Crosignani et al; Human Reprod, 2006, 248-256, 21.
Dassen et al; Human Reprod, 2007, 3148-3158, 12.
Del Frate et al; RadioGraphics, 2006, 1705-1718, 26. Ebert et al; Obstet Gynecol, 2005, 144-150, 122.
Fang et al; Fertility and Sterility, 2004, 673-678, 82.
Gurates et al; Seminar in Reprod Med, 2003, 125-134, 21.
Hastings et al; Reprod Biol Endo, 2006, S7, 4.
Heiler et al; Fertility and Sterility, 2006, 1516-1518, 85.
Ishihara et al; Fertility and Sterility, 2003, 735-42, 79.

(Continued)

*Primary Examiner* — Shengjun Wang
*Assistant Examiner* — Samira Jean-Louis

(57) ABSTRACT

The invention relates to a method of treating endometriosis using a combination of an aromatase inhibitor, a progestin and an oestrogen. The invention also relates to pharmaceutical formulations comprising said combination.

3 Claims, No Drawings

OTHER PUBLICATIONS

Kyama et al; Fertility and Sterility, 2008, 301-310, 89.
Meresman et al; Fertility and Sterility, 2005, 459-463, 84.
Mukakami et al, Fertility and Sterility, 2006, 291-297, 86.
Nobel et al; J Clin Endo Metab, 1996, 174-179, 81.
Nobel et al; J Clin Endo Metab, 1997, 600-606, 82.
Sharpe-Timms et al; NY Acad Sci, 2001, 131-147, 943.
Simpson et al; NY Acad Sci, 2001, 58-67, 949.
Smuc et al; Gynecol Endo, 2007, 105-111, 23.
Velasco et al; Molec Human Reprod, 2006, 377-381, 12.
Wu et al; Am J Pathol, 2005, 1061-1069, 167.
Banu et al., Short title: COX-2 in endometriosis, 2007, 1-29.
Falconer et al., Endometriosis and Genetic Polymorphisms, 2007, 616-628, 62.
Sharp-Timms et al., Using rats as a Research Model for the study of endometriosis, 318-327.
Yano et al., Studies on the Effect of the New Non-steroidal Aromatase Inhibitor Fadrozole Hydrochloride in an Endometriosis Model in Rats, 1996, 192-195, 46.
Yue et al; Cancer Res, 1998, 927-932, 58.
Zeitoun et al; Fertility and Sterility, 1999, 961-969, 72.
Zeitoun et al; Molec Endocrin, 1999, 239-253, 13.
English Language Translation of Portion of Nov. 19, 2009 Office Action for Corresponding Japanese Patent Application No. 2006-502229 Relevant to References Cited Therein.
Takayama, K. et al., "Treatment of Severe Postmenopausal Endometriosis with an AromataseInhibitor", Fertility and Sterility, Apr. 1998, vol. 69, No. 4, pp. 709-713.
Asada, H. et al., "Medical Management of Endometriosis-Associated Infertility and Endometriosis Associated Pain", Sanfujinka Chiryo (Obstetrical and Gynecological Therapy), Oct. 1, 2001, vol. 83, No. 4, pp. 443-450.
Uemura, T. et al., "Current Situation of Medical Care for Endometriosis: Chemotherapy for Endometriosis" Sanka To Fujinka (Obstetrics and Gynecology Tokyo), Aug. 1987, vol. 54, No. 8, pp. 1457-1463.
Archer, D. F. et al., "A New Low-Dose Monophasic Combination Oral Contraceptive (AlesseTM) with Levonorgestrel 100 μg and Ethynyl Estradiol 20 μg", Contraception, Mar. 1997, vol. 55, No. 3, pp. 139-144.
Fang, Z et al 'Genetic or Enzymatic Disruption of Aromatase Inhibits the Growth of Ectopic Uterine Tissue' Journal of Clinical Endocrinology & Metabolism, 2002, pp. 3460-3466, vol. 87(7).
Rice, V, M. 'Conventional Medical Therapies for Endometriosis' Annals of the New York Academy of Sciences, 2002, pp. 343-352, vol. 955.
Olive, D, L & Pritts, E, A 'Treatment of Endometriosis' New England Journal of Medicine, 2001, pp. 266-275, vol. 345(4).
Bulun, S, E et al 'Molecular basis for treating endometriosis with aromatase inhibitors' Human Reproduction Update, 2000, pp. 413-418, vol. 6(5).
Zumpe, D et al 'Behavioural responses to depo-provera, fadrozole, and estradiol in castrated, testosterone-treated cynomolgus monkeys (*Macaca fascicularis*): the involvement of progestin receptors' Physiology and Behaviour, 1996, pp. 531-540, vol. 60/2.
Bulun, S, E et al 'Aromatase as a therapeutic target in endometriosis' Trends in Endocrinology and Metabolism, 2000, pp. 22-27, vol. 11(1).
Surrey, E et al 'Prolonged GnRH agonist and add-back therapy for symptomatic endometriosis: long-term follow-up' Obstet & Gynecol, 2002, pp. 709-719, vol. 99(5).
Mahutte, N, G et al 'Medical management of endometriosis-associated pain' Obstetrics and Gynecology Clinics of North America, 2003, pp. 133-150, vol. 30/1.
Genazzani, A, R et al 'Hormone replacement therapy and cancer. International menopause society workshop' Gynecological Endocrinology, 2001, pp. 453-465, vol. 15/6.
Ailawadi Radhika, K et al 'Treatment of endometriosis and chronic pelvic pain with letrozole and norethindrone acetate: A pilot study' Fertility and Sterility, 2004, pp. 290-296, vol. 81(2).

* cited by examiner

COMPOSITION COMPRISING A COMBINATION OF AN AROMATASE INHIBITOR, A PROGESTIN AND AN OESTROGEN AND ITS USE FOR THE TREATMENT OF ENDOMETRIOSIS

CROSS-REFERENCE TO RELATED APPLICATIONS

This application is a US National Stage under 35 U.S.C §371 of International Application No. PCT/GB2004/000414 (filed Feb. 3, 2004) which claims priority under 35 U.S.C. §119(a)-(d) to Application No. GB0302572.3 filed on Feb. 5, 2003.

The present invention relates to a method of treating endometriosis using a combination of an aromatase inhibitor, a progestin and an oestrogen. The invention also relates to pharmaceutical formulations comprising said combination.

Endometriosis is characterised by the presence of endometrial-like tissue outside the uterine cavity and is largely a condition seen in premenopausal women. It is estimated to affect between 2-10% of women of child-bearing age. This endometrial-like tissue responds in the same way as the normal endometrium to changes in the hormonal environment during the menstrual cycle so that as the concentrations of oestrogen and progesterone change, the tissue grows and is shed in the same way as the endometrium itself. Symptoms of endometriosis include pelvic pain, dysmenorrhoea and dyspareunia and it is often found in association with infertility although its exact relationship to infertility, except in severe endometriosis, is uncertain. [For a general review of endometriosis and current treatment strategies the user is referred to: Olive D L. Pritts E A. (2001) New England Journal of Medicine. 345(4):266-75]. Both medical and surgical approaches and a combination of the two are used in an attempt to eradicate the disease, however, in many instances treatment is not curative and the disease and its associated symptoms return.

Oestrogen is the most well-defined mitogen that enhances growth and inflammation in this extra-uterine tissue giving rise to increased pelvic pain. Treatments that inhibit the production of the major source of oestrogen in premenopausal women, namely the ovaries, or which create a so-called pseudomenopause have been used to successfully treat endometriosis. In the former class, the gonadotrophic hormone releasing hormone agonist analogues (GnRH analogues) inhibit the production of LH and to a lesser extent FSH from the pituitary gland leading to inhibition of the production of oestradiol by the ovaries. This lowering of circulating oestradiol concentrations into the postmenopausal range results in an improvement of pelvic pain and pressure symptoms and regression of endometrial implants. Danazol and progestogenic agents are also used to treat the disease. Treatment with the GnRH analogues although effective is limited to 6 months because of the potential effects on bone mineral density. Treatment with danazol is also limited because of its androgenic side-effects.

Not infrequently, patients may not tolerate and/or respond to currently available medical approaches. Additionally, there is a high incidence of recurrence.

For example, 18 months after completing a 6-month course of Lupron™-depot (which contains the GnRH agonist leuprolide), only 52% of patients had significant relief of pain. The recurrence rate of pain in the rest of the patients was approximately 5-20% per year (reaching a cumulative average rate at 5 years as high as 53%). The recurrence rate at 5 years was as high as 75% in severe forms of endometriosis [see Rice V M (2002) Annals of the New York Academy of Sciences 955:343-352]. In women treated for pelvic pain, the symptoms usually return rather quickly after cessation of therapy. For a period of time after medical treatment, however, the intensity of symptoms is less severe. The recurrence rates after treatment with GnRH agonists are similar to those after danazol, and both are similar to those obtained with surgical excision.

Recent work has demonstrated that other sources of oestrogen, in addition to the ovaries, contributes to the development and continued presence of endometriosis. In particular, high levels of local aromatase activity and oestrogen production within the endometriotic tissue per se appear central to the maintenance and pathophysiology of endometriosis. Thus, aromatase inhibitors have been suggested for the treatment of endometriosis [Bulun et al (2000) Human Reproduction Update 6(5), 413-418; Bulun et al (2000) Trends in Endocrinology and Medicine 11(1), 22-27].

Given continuously GnRH analogues by inhibiting the production of gonadotrophins from the pituitary gland, reduce circulating oestradiol concentrations into the postmenopausal range. Aromatase inhibitors would not be expected to lower serum oestradiol concentrations, however, in pre-menopausal women because of the feedback mechanism, the hypothalamic-pituitary axis, so that when circulating oestradiol concentrations fall the pituitary gland produces more gonadotropins, which in turn stimulate the production of oestrogen by the ovaries. It has been hypothesised that the increased concentrations of the gonadotrophin, follicle stimulating hormone (FSH) may result in the formation of cysts in the ovary. The concomitant use of a progestin agent with the aromatase inhibitor would be expected to diminish this surge in pituitary gonadotropins. Another benefit of the concomitant administration of a progestin is that it would be expected to directly cause thinning of the eutopic endometrium due to the dominant progestogenic effect.

Although oestrogen has a pathological role in endometriosis, it also has a protective effect in a number of tissues, such as bone. Thus, treatment of endometriosis with oestrogen lowering therapies may have side effect due to inhibition of the protective effects of oestrogen in addition to inhibition of the pathological effects of oestrogen. For examples treatment of endometriosis with GNRH analogues leads to castrate levels of oestrogen resulting in side effects including transient vaginal bleeding, hot flashes, vaginal dryness, decreased libido, breast tenderness, insomnia, depression, irritability and fatigue, headache, osteoporosis, and decreased elasticity of the skin.

Thus, strategies that inhibit the oestrogen driven symptoms of endometriosis with minimal side effects are required. The combination of an aromatase inhibitor with a progestin would be expected to have some advantage in relation to bone loss. However, the further addition of an oestrogen to this combination would not only prevent bone loss more effectively than the addition of a progestin alone, but would also be expected to stop breakthrough bleeding commonly seen with progestins. However, the addition of an oestrogen to patients with endometriosis in combination with the partial oestrogen-reducing therapy of an aromatase inhibitor in premenopausal women would be expected to exacerbate the condition or reduce the efficacy of treatment with the aromatase inhibitor. Indeed, using an endometriosis model in studies in wild type mice and aromatase knockout mice Fang et al found that the addition of oestrogen to the aromatase inhibitor letrozole resulted in increases in the endometriotic lesion sizes and thus exacerbates the endometriosis [Fang et al (2002) Journal of Clinical Endocrinology & Metabolism 87(7), 3460-3466].

We have studied the combination of an aromatase inhibitor, a progestin and an oestrogen and we have surprisingly found that the addition of an oestrogen to the combination of an aromatase inhibitor and a progestin, contrary to expectations, results in effective palliation of symptoms in women with severe endometriosis. Furthermore, this combination therapy was well tolerated with only mild hot flashes, breakthrough spotting and no significant changes between baseline and post-treatment hip and spine bone densitometry measurements.

Thus, according to the first aspect of the invention there is provided a method of treatment of endometriosis comprising the administration of a combination of an aromatase inhibitor, a progestin and an oestrogen.

According to a further aspect of the invention there is provided the use of a combination of an aromatase inhibitor, a progestin and an oestrogen in the manufacture of a medicament for the treatment of endometriosis.

According to a further aspect of the invention there is provided a pharmaceutical composition comprising a combination of an aromatase inhibitor, a progestin and an oestrogen in admixture with a pharmaceutically-acceptable diluent or carrier for the treatment of endometriosis.

For the avoidance of doubt in such a pharmaceutical composition the components may be formulated as follows:
(i) the aromatase inhibitor, progestin and oestrogen mixed together in a single formulation;
(ii) two of the components mixed together in a single formulation and one component formulated separately, for simultaneous or sequential dosing; or
(iii) each component formulated separately, for simultaneous or sequential dosing.

In this specification an aromatase inhibitor is defined as a compound that prevents oestrogens from being formed from their metabolic precursors by inhibiting the enzyme aromatase. Examples of aromatase inhibitors include:
(i) the testolactone (17a-oxa-D-homoandrost-1,4-diene-3,17-dione) that is described in the "Journal of Clinical Endocrinology and Metabolism," 49, 672 (1979);
(ii) the compounds androsta-4,6-diene-3,17-dione, androsta4,6-dien-17.beta.-ol-3-one acetate, androsta-1,4,6-triene-3,17-dione, 4-androstene-19-chloro-3,17-dione, 4-androstene-3,6,17-trione that are described in "Endocrinology" 1973, Vol. 92, No. 3, page 874,
(iii) the 19-alknylated steroids that are described in German patent application number DE 3124780,
(iv) the 10-(1,2,-propadienyl)-steroids that are described in German patent application number DE 3124719,
(v) the 19-thio-androstane derivatives that are described in European patent application, publication no. EP 100566,
(vi) the 4androsten-4-ol-3,17-dione and its esters that are described in "Endocrinology" 1977, Vol. 100, No. 6, page 1684 and U.S. Pat. No. 4,235,893,
(vii) the 1-methyl-15.alpha.-alkyl-androsta-1,4-diene-3,17-dione that is described in German patent application number DE 3539244,
(viii) the 10.beta.-alkinyl4,9(11)-estradiene derivatives that are described in German patent application number DE 3644358 and
(ix) the 1,2.beta.-methylene-6-methylene4-androstene-3,17-dione that is described in European Patent Application EP 250 262.

Further examples of aromatase inhibitors include: atamestane, formestane, fadrozole, letrozole, pentrozole, anastrozole and vorozole.

A more preferred aromatase inhibitor is anastrozole. Anastrozole can be administered at a dose and/or schedule to deliver between 0.1 and 10 mg/day, preferably, between 0.5 and 5 mg/day, most preferably anastrozole is administered at 1 mg/day.

In this specification a progestin is defined as a natural or synthetic progestational substance that mimics some or all of the actions of progesterone. Examples of progestins include derivatives of 19-nortestosterone, such as oestranes and gonanes, and derivatives of 17α-acetoxyprogesterone (pregnanes). Examples of oestranes include: norethindrone and its acetates, and ethynodiol diacetate. Examples of gonanes include norgestrel and levonorgestrel and the less androgenic derivatives of levonorgestrel such as desogestrel, norgestimate, and gestodene. Further examples of progestins include norgestrel, levonorgestrel, norethindrone, norethindrone acetate, desogestrel, norgestimate and ethynodiol diacetate. A preferred progestin is levonorgestrel. Levonorgestrel can be administered at a dose and/or schedule to deliver between 0.05 and 0.15 mg/day, preferably 0.1 mg/day.

In this specification oestrogens are defined as compounds which has agonist activity at the oestrogen receptor. Partial agonists and full agonists are envisaged but full agonists are preferred. An example of a partial agonist is tamoxifen. Examples of full agonists include oestrogen, oestradiol, mestranol and ethinyl oestradiol. Further examples of full agonists include oestrogen, oestradiol and ethinyl oestradiol. Preferred oestrogens include ethinyl oestradiol and mestranol. A more preferred oestrogen is ethinyl oestradiol. Ethinyl oestradiol can be administered at a dose and/or schedule to deliver between 0.01 and 0.06 mg/day, preferably 0.02 mg/day.

Conveniently the progestin and oestrogen components of the combination of the invention could be provided by a combination birth control pill comprising an oestrogen and a progestin. Examples of such birth control pills include tablets comprising:
(i) ethinyl oestradiol and norethindrone;
(ii) ethinyl oestradiol and norgestimate;
(iii) ethinyl oestradiol and desogestrel;
(iv) ethinyl oestradiol and levonogestrel;
(v) ethinyl oestradiol and gestodene;
(vi) ethinyl oestradiol and norgestrel; and
(vii) mestranol and norethindrone.

A preferred combination birth control pill comprises ethinyl oestradiol and levonogestrel.

In one aspect of the invention, the administration is carried continuously, for at least 6 months. However, treatment for 1 to 2 years is also envisaged. Treatment for greater than 2 years is also contemplated.

Treatment of pre-menopausal women is most preferred, however treatment of post-menopausal women would also be contemplated in those women for whom oestrogen replacement therapy would be considered yet currently thought contraindicated due to concerns regarding endometriosis.

In another aspect the combination of the invention is contemplated for patients who are refractory to a combination of surgical resection and/or one or more course of prior or subsequent hormonal treatment. Examples of such hormonal therapy include treatment with GnRH analogues.

The term 'surgical resection' refers to surgical removal of endometriotic implants and/or lysis of adhesions caused by scarring from endometriosis. Such removal could comprise ablation by for example a laser.

In order to carry out the invention the combination could be provided in a single formulation or in multiple formulations, comprising one or more of the components of the combination. Administration of the elements of the combination could be administered simultaneously or each component could be administered at different times. Simultaneous administration is preferred. The combination may be provided in various formulations such as parentally (e.g. aqueous or oily suspensions) or orally (e.g., tablets, powders, capsules, granules, aqueous or oily suspensions). Preferably, the combination is provided in an orally available formulation to be administered daily. However, slow release formulation or depot or transdermal formulations could also be used to administer the combination.

Thus, according a further feature of the invention there is provided a pharmaceutical formulation comprising an aromatase inhibitor, a progestin and an oestrogen, preferably a pharmaceutical formulation for the treatment of endometriosis.

For preparing pharmaceutical formulations of the invention, inert, pharmaceutically acceptable carriers can be added to the components of the composition which can either be solid or liquid Solid form preparations include powders, tablets, dispersible granules, capsules and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

Suitable carriers include magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term formulation is intended to include the mixture of the active component with encapsulating material as a carrier providing a capsule in which the active component (with or without other carriers) is surrounded by a carrier which is thus in association with it. Similarly, cachets are included. Tablets, powders, cachets, and capsules can be used as solid dosage forms suitable for oral administration.

Liquid form compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution. Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

The pharmaceutical formulation can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

The invention will now be illustrated with reference to the following non-limiting example.

A clinical trial was designed to assess the efficacy of a combination of an aromatase inhibitor, a progestin and an oestrogen in the treatment of endometriosis. 18 patients with severe endometriosis-related pelvic pain, who previously have not responded to a combination of surgical resection and one or more courses of hormonal treatment were included in the trial. The patients had an age range of 23 to 46, and all patients had normal ovarian function. These patients were treated with the oral aromatase inhibitor, anastrozole [Arimidex™] at 1 mg/day in combination with an oestrogen-containing birth control pill, Alesse 21™ one tablet per day [Alesse 21™ contains levonorgestrel (0.1 mg), a progestin and ethinyl oestradiol (0.02 mg), an oestrogen]. Patients were assessed for severity of pain and for severity of side effects. Of these 18 patients, 9 patients completed the study.

Pain

A self-assessment visual analog pain scoring system (VAS), varying in severity from 0 (no pain) to 10 (maximum pain) was used, which was recorded daily. All patients had baseline pain scores between 7 and 10. Tables 1 and 2 show the results of the pain measurements in the trial. Table 1 shows the data for the 9 patients who completed the study, Table 2 shows the data for all the patients in the study, the number of patients at each time point is indicated. The results show a significant decrease in pain in the patients at each time point, with an increase in pain relief up to the final 6 month time point.

TABLE 1

Average Monthly Pain Scores for the 9 patients that completed the study Statistical significance was assessed by ANOVA followed by Newman-Keuls multiple comparisons test

|  | Mean Pain Score | Statistical Significance vs pre-treatment | Statistical Significance vs $1^{st}$ month |
|---|---|---|---|
| Pre-treatment | 8.6 | | |
| $1^{st}$ month | 6.1 | $p < 0.01$ | |
| $2^{nd}$ month | 5.3 | $p < 0.001$ | $p < 0.05$ |
| $6^{th}$ month | 4.6 | $p < 0.0005$ | |

TABLE 2

Average Monthly Pain Scores for all patients in trial

|  | Mean Pain Score[1] | Number of patient |
|---|---|---|
| Pre-treatment | 8.3 | 15 |
| $1^{st}$ month | 5.8 | 14 |
| $2^{nd}$ month | 5.2 | 14 |
| $6^{th}$ month | 4.6 | 9 |

[1]All results showed statistical significance between each other.

Side Effects

Side effects were captured in the scheduled office visits and recorded in patient charts. Potential side effects which were monitored included lack of tolerability (i.e. lack of hypoestrogenemic symptoms, for example those associated with GnRH treatment such as transient vaginal bleeding, hot flashes, vaginal dryness, decreased libido, breast tenderness, insomnia, depression, irritability and fatigue, headache, osteoporosis, breakthrough spotting and decreased elasticity of the skin) and safety issues (i.e. no surge in gonadotropins leading to ovarian stimulation and cyst formation and preserved bone densitometry measurements).

The most consistently observed side effects were mild hot flashes and breakthrough spotting, although breakthrough spotting occurred in a few patients almost exclusively as a result of inadvertent interruptions of the oestrogen-containing birth control pill.

No significant changes were detected between baseline and post treatment DEXA bone densitometry measurements of the hip and spine.

Monthly measurements of FSH, LH, oestradiol and oestrone did not show significant alterations from the baseline. Thus no surge in gonadotropins was observed.

Thus, the combination of an aromatase inhibitor, oestrogen and progestin results in an efficaceous treatment of the symptoms of endometriosis, with a relatively benign side effect profile.

The invention claimed is:

1. A method of treating endometriosis comprising simultaneously administering to a premenopausal woman in need thereof daily doses of a combination of 0.1 to 10 mg of anastrozole, 0.05 mg to 0.15 mg of levonorgestrel, and 0.01 mg to 0.06 mg of ethinyl oestradiol.

2. The method of claim 1, wherein said daily doses are administered continuously for at least one month.

3. The method of claim 1, wherein said premenopausal woman is refractory to one or more courses of prior hormonal treatment.

* * * * *